(12) United States Patent
Roney, Jr. et al.

(10) Patent No.: US 7,779,709 B2
(45) Date of Patent: Aug. 24, 2010

(54) METHODS AND APPARATUS FOR ROTARY MACHINERY INSPECTION

(75) Inventors: Robert Martin Roney, Jr., Schoharie, NY (US); Thomas Francis Murphy, Scotia, NY (US); Richard Michael Hatley, Convent Station, NJ (US)

(73) Assignee: General Electric Company, Schenectady, NY (US)

( * ) Notice: Subject to any disclaimer, the term of this patent is extended or adjusted under 35 U.S.C. 154(b) by 681 days.

(21) Appl. No.: 11/256,423

(22) Filed: Oct. 21, 2005

(65) Prior Publication Data

US 2007/0089546 A1   Apr. 26, 2007

(51) Int. Cl.
*G01M 19/00* (2006.01)
(52) U.S. Cl. .................................... 73/865.8
(58) Field of Classification Search ................ 73/865.8, 73/104; 250/302
See application file for complete search history.

(56) References Cited

U.S. PATENT DOCUMENTS

| | | | | |
|---|---|---|---|---|
| 2,011,408 A | * | 8/1935 | Jacobs | 324/216 |
| 2,806,959 A | * | 9/1957 | De Forest et al. | 250/302 |
| 3,421,694 A | * | 1/1969 | Muller | 239/142 |
| 3,607,784 A | * | 9/1971 | Mlot-Fijalkowski | 252/408.1 |
| 3,762,216 A | * | 10/1973 | Mendoza | 73/104 |
| 3,916,032 A | * | 10/1975 | Conner | 427/8 |
| 4,113,182 A | * | 9/1978 | Brago | 239/304 |
| 4,968,892 A | * | 11/1990 | McAtee | 250/458.1 |
| 5,115,136 A | * | 5/1992 | Tomasch | 250/461.1 |
| 5,281,487 A | | 1/1994 | Rumaner et al. | 428/552 |
| 5,574,213 A | * | 11/1996 | Shanley | 73/40.7 |
| 5,830,586 A | | 11/1998 | Gray et al. | 428/621 |
| 5,897,921 A | | 4/1999 | Borom et al. | 427/454 |
| 5,914,189 A | | 6/1999 | Hasz et al. | 428/335 |
| 5,989,343 A | | 11/1999 | Borom et al. | 118/308 |
| 6,022,594 A | | 2/2000 | Borom et al. | 427/453 |
| 6,047,539 A | | 4/2000 | Farmer | 60/775 |
| 6,432,487 B1 | | 8/2002 | Graham et al. | 427/454 |
| 6,706,325 B2 | | 3/2004 | Spitsberg et al. | 427/255.19 |
| 6,740,364 B2 | | 5/2004 | Lau et al. | 427/452 |

* cited by examiner

*Primary Examiner*—Hezron Williams
*Assistant Examiner*—Tamiko D Bellamy
(74) *Attorney, Agent, or Firm*—Armstrong Teasdale LLP

(57) ABSTRACT

Methods and systems for an in-situ inspection system includes at least one source of an inspection fluid, a source of an atomizing fluid, a control panel configured to control a flow of at least one of the inspection fluid and the atomizing fluid, and a mixing box configured to mix the inspection fluid with the atomizing fluid.

21 Claims, 4 Drawing Sheets

500

502
Positioning an outlet of an inspection fluid wand proximate a component to be inspected

504
Selecting an inspection fluid source from a plurality of inspection fluid sources

506
Initiating a flow of at least one of an atomizing fluid and an inspection fluid to a mixing box in flow communication with the inspection fluid wand

508
Channeling a flow of atomized inspection fluid to the component to be inspected

FIG. 5

METHODS AND APPARATUS FOR ROTARY MACHINERY INSPECTION

BACKGROUND OF THE INVENTION

This application relates generally to gas turbine engines and, more particularly, to methods and apparatus for testing gas turbine engine compressor and turbine rotor assemblies.

At least some known gas turbine engines include a compressor for compressing air, which is mixed with a fuel and channeled to a combustor wherein the mixture is ignited within a combustion chamber for generating hot combustion gases. The hot combustion gases are channeled downstream to a turbine, which extracts energy from the combustion gases for powering the compressor, as well as producing useful work to propel an aircraft in flight or to power a load, such as an electrical generator.

Known compressors include a rotor assembly that includes at least one row of circumferentially spaced rotor blades. Each rotor blade includes an airfoil that includes a pressure side and a suction side connected together at leading and trailing edges. Each airfoil extends radially outward from a rotor blade platform. Each rotor blade also includes an attachment portion, such as, a dovetail that extends radially inward from the platform, and is used to mount the rotor blade within the rotor assembly to a rotor disk or spool. More specifically, at least some known rotor disks include a plurality of circumferentially spaced axially oriented dovetail slots that are sized to receive a respective one of the plurality of rotor blades therein.

During operation, the rotor blades may be subjected to environmental and loading forces that may cause in-service cracking of the blades. Known inspection techniques are limited in their ability to assess the integrity of the blades while the blades are in-place. More specifically, a visual inspection only permits a limited examination of the blades for cracks in the airfoil and in a very limited area of the dovetail. To thoroughly examine the blades where cracking may originate, at least a portion of the engine casing may need to be removed to facilitate removal of each blade, and subsequent inspection of the dovetails with visual, magnetic particle, or liquid penetrant techniques. However, because of labor and cost constraints such techniques may be impracticable in some instances.

BRIEF DESCRIPTION OF THE INVENTION

In one embodiment, an in-situ inspection system includes at least one source of an inspection fluid, a source of an atomizing fluid, a control panel configured to control a flow of at least one of the inspection fluid and the atomizing fluid, and a mixing box configured to mix the inspection fluid with the atomizing fluid.

In another embodiment, a dye penetrant test system includes a source of a plurality of inspection fluids, a flow control associated with each of the plurality of inspection fluids, and a mixing box configured to atomize a selected at least one of the plurality of inspection fluids.

In yet another embodiment, a method of dye penetrant testing is provided. The method includes positioning an outlet of an inspection fluid wand proximate a component to be inspected, selecting an inspection fluid source from a plurality of inspection fluid sources, initiating a flow of at least one of an atomizing fluid and an inspection fluid to a mixing box in flow communication with the inspection fluid wand, and channeling a flow of atomized inspection fluid to the component to be inspected.

BRIEF DESCRIPTION OF THE DRAWINGS

FIG. 5 is a flow chart of an exemplary method of dye penetrant testing that may be used to test and/or inspect the blades shown in FIG. 3.

DETAILED DESCRIPTION OF THE INVENTION

Figure 1:
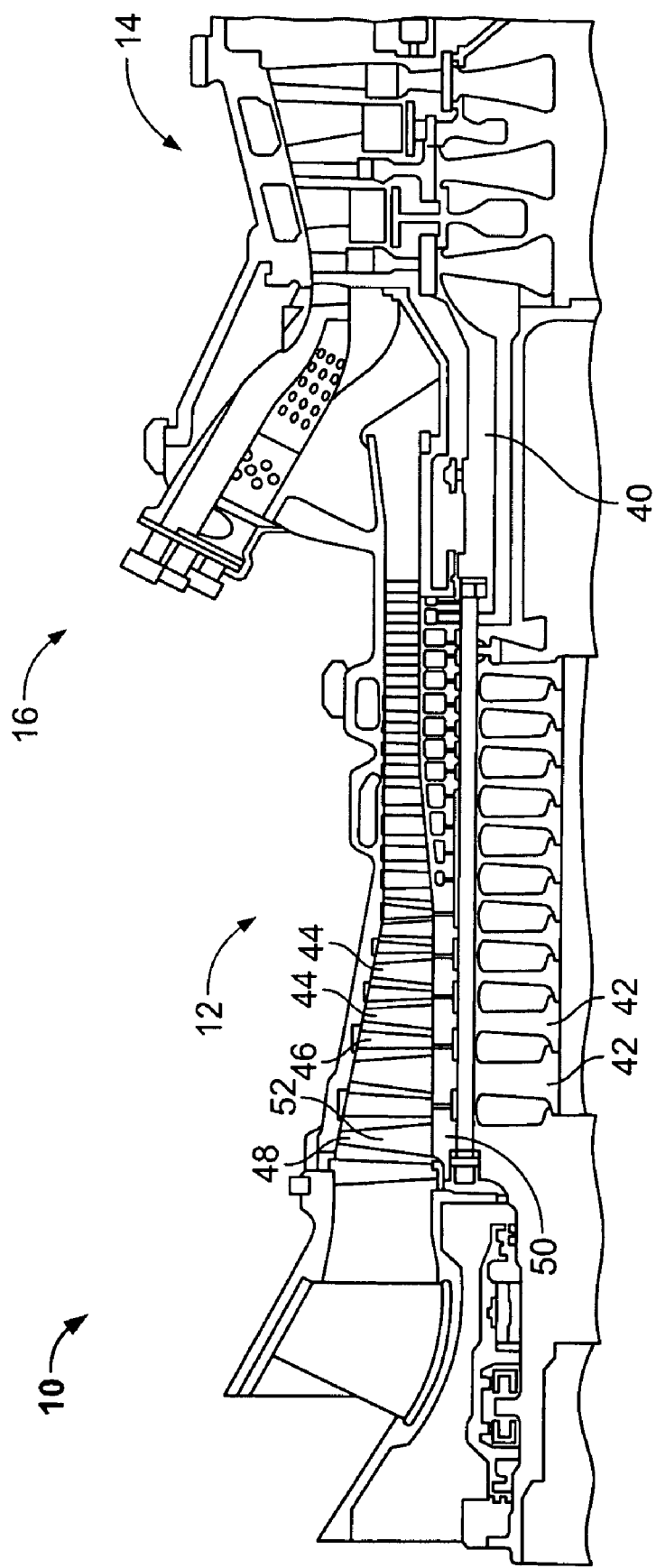
FIG. 1 is a side elevation view of an exemplary gas turbine engine.

FIG. 1 is a side elevation view of an exemplary gas turbine engine 10 that includes a compressor section 12, a turbine section 14 and a plurality of combustors 16 (only one combustor shown in FIG. 1) Engine 10 includes a rotor 40 including a plurality of rotor wheels 42. Each rotor wheel 42 is configured to mount a plurality of components, such as, but not limited to, buckets or blades 44, which in conjunction with a respective number of stator vanes 46, form the various stages of engine 10. In the exemplary embodiment, a plurality of compressor blades 44 are coupled to a first row 48 that includes a first-stage rotor wheel 50. Each blade 44 includes an airfoil 52 that is mounted in opposition to respective first-row stator vanes 54. Blades 44 are spaced circumferentially about first-stage wheel 50. Turbine engine 10 may drive a generator (not shown) for producing electrical power. In the exemplary embodiment, engine 10 is a MS6001B gas turbine engine, commercially available from General Electric Company, Greenville, S.C.

Figure 2:
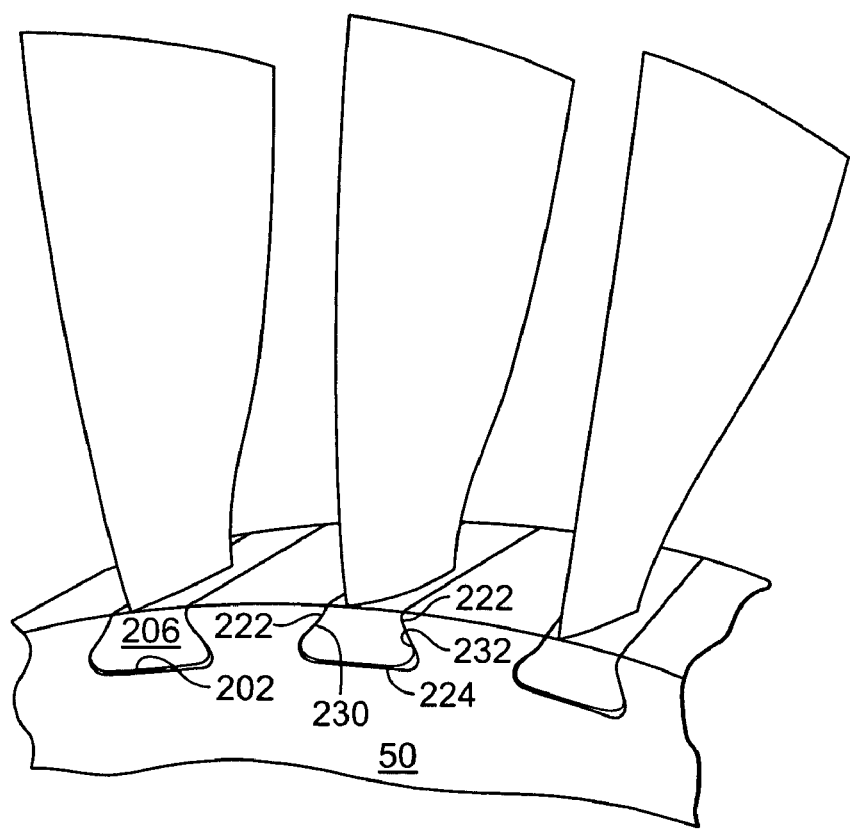
FIG. 2 is a perspective view of a portion of first stage rotor wheel that may be used with the gas turbine engine shown in FIG. 1.

FIG. 2 is a perspective view of a portion of first stage rotor wheel 50. Rotor wheel 50 includes a plurality of axially aligned dovetail slots 202 that are spaced circumferentially about a radially outer periphery of wheel 50. Slots 202 receive an attachment portion, such as a dovetail 206 of blade 44, therein. More specifically, blades 44 are removably coupled within disk slot 202 by each respective blade dovetail 206. Accordingly, slot 202 is shaped to generally compliment a shape of each dovetail 206 received therein, and accordingly, in the exemplary embodiment, includes a pair of wheel post tangs 222 and a disk slot bottom 224 that extends between wheel post tangs 222. In the exemplary embodiment, disk slot 202 also includes a pair of opposed wheel faces 230 and 232.

Figure 3:
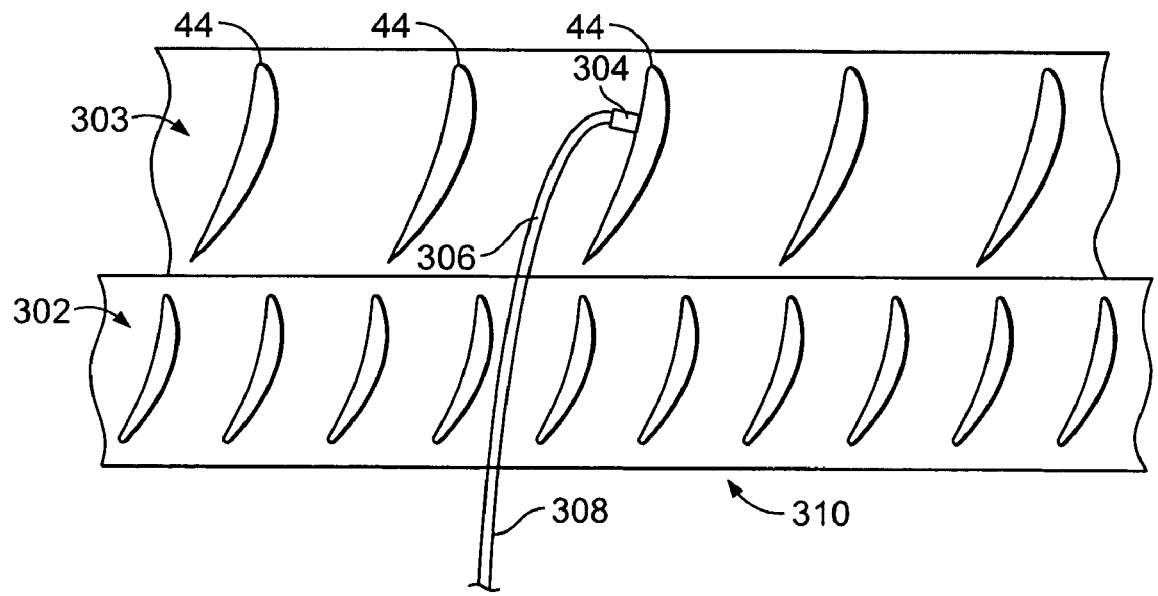
FIG. 3 is a radial perspective view of a row of inlet guide vanes (IGV) and a row of blades that may be used with the gas turbine engine shown in FIG. 1.

FIG. 3 is a radial perspective view of an exemplary row of inlet guide vanes (IGV) 302 and a row 303 of blades 44 that may be used with gas turbine engine 10 (shown in FIG. 1). In the exemplary embodiment, a test head 304 is positioned proximate at least one of the blades 44 and a length of spray tubing 306 extends from test head 304 to a supply end 308 in an accessible area 310 upstream from inlet guide vanes 302. Spray tubing 306 is configured to extend between inlet guide vanes 302 to access blades 44 in row 303. Spray tubing 306 is also configured to extend between row 303 to access a second row of blades (not shown) downstream from row 303.

Figure 4:
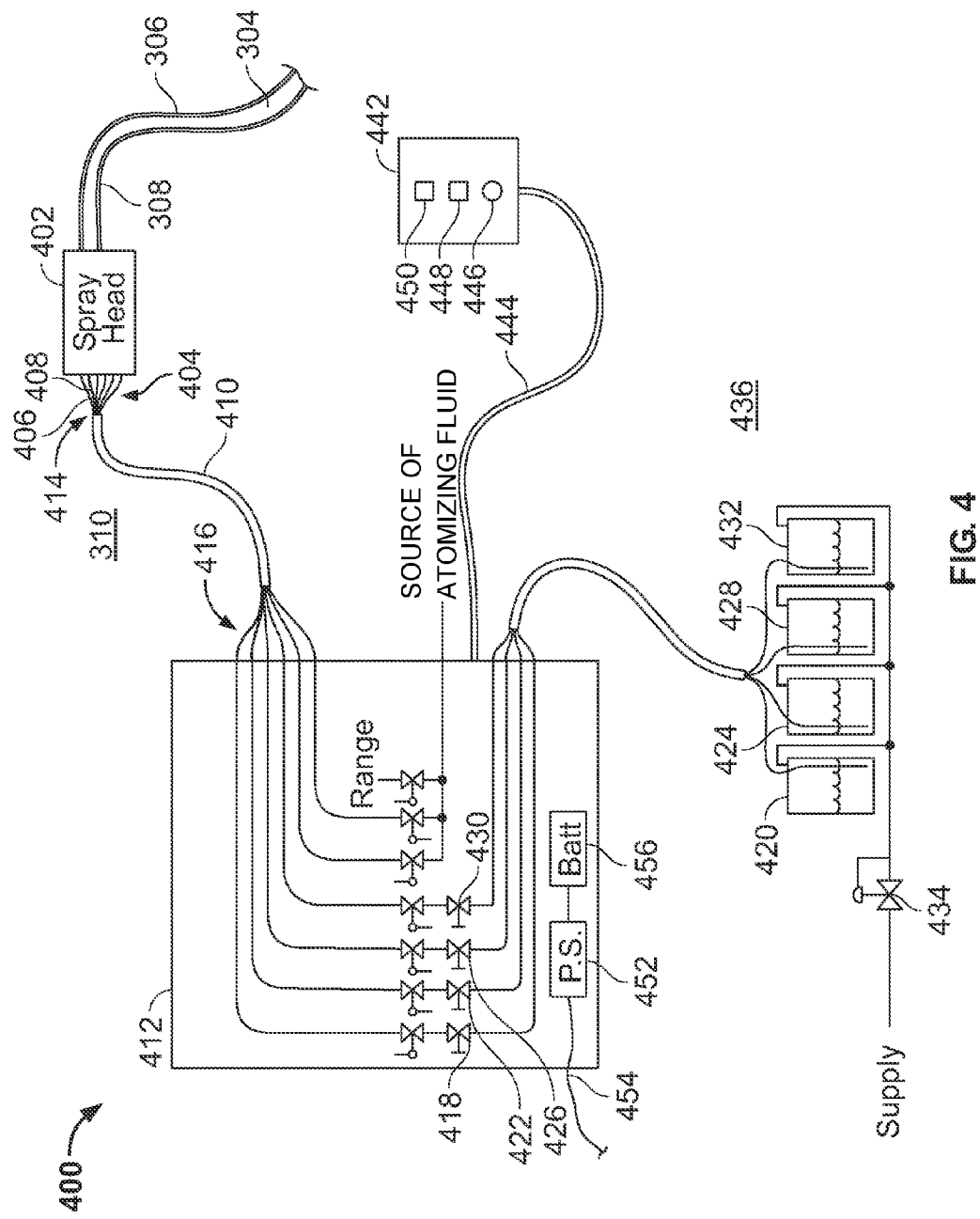
FIG. 4 is an exemplary embodiment of a penetrant test control system that may be used with the row of blades shown in FIG. 3.

FIG. 4 is a schematic block diagram of a penetrant test system 400 that may be used to test and/or inspect blades 44 (shown in FIG. 3). In the exemplary embodiment, supply end 308 is coupled to a spray head 402 that is configured to receive a flow of test fluids through a plurality of inlet tubes 404, a flow of atomizing fluid through an atomizing tube 406 and a flow of drying fluid through a drying tube 408. Spray head 402 is configured to combine the flow from one or more of inlet tubes 404 with the flow from atomizing tube 406 in a predetermined proportion such that an atomized stream of test fluid exits spray head 402 and is channeled to blade 44 proximate test head 304. A flow of drying fluid is configured to pass through spray head 402 and spray tubing 306 to dry blade 44 during a step of a test procedure.

A spray manifold 410 couples spray head 402 in flow communication with a control box 412. Spray manifold includes a plurality of tubes 404, 406, and 408, each configured to couple to spray head 402 on a first end 414 and to control box 412 on a second end 416. Within control box 412, each of tubes 404, 406, and 408 couple to a respective control valve. In the exemplary embodiment, the control valves are solenoid operated valves. In an alternative embodiment, the valves are controlled by other than a solenoid, for example, pneumatically. Each of inlet tubes 404 that carry test fluids are serially coupled to a respective flow control valve and each flow control valve is coupled to a source of test fluid. In the exemplary embodiment, a flow control valve 418 is coupled to a first source 420 of test fluid, such as a cleaning solvent, a flow control valve 422 is coupled to a second source 424 of test fluid, such as a penetrant dye, a flow control valve 426 is coupled to a third source 428 of test fluid, such as a rinsing agent, and a flow control valve 430 is coupled to a fourth source 432 of test fluid, such as a developer.

In the exemplary embodiment, test fluid sources 420, 424, 428, and 432 are pressurized using pressurized air from, for example, a facilities service air header. An air pressure regulator 434 maintains a constant air pressure within test fluid sources 420, 424, 428, and 432. In an alternative embodiment, test fluid sources 420, 424, 428, and 432 are vented to ambient 436 and the test fluids contained therein are educted to supply the test fluids to system 400. As such, test fluids sources 420, 424, 428, and 432 are either selectively pressurized prior to being selected, or are educed by system 400 to flow through respective flow control valves 418, 426, and 430.

A remote pendant 440 is communicatively coupled to control box 412 through a cable 444. Remote pendant 442 includes a selector 446 for selecting a source of test fluid to be used during a test procedure, an "on" pushbutton 448 to actuate the valves to fluidly couple the selected test fluid to spray head 402, and a purge pushbutton 450 to supply a clear stream of fluid, for example, pressurized air, to clear the test fluid flowpath to avoid having a buildup in the flowpath block the flowpath. In the exemplary embodiment, selector 446 is a multi-position rotary selector switch and each of pushbuttons 448 and 450 are momentary contact pushbutton switches.

During a test procedure, test head is positioned proximate a workpiece to be tested, such as turbine blade 44 that is limitedly accessible from accessible area 310. Blade 44 is cleaned by selecting first source 420, which, in the exemplary embodiment, includes a quantity of solvent or cleaner. Source 420 is pressurized to a predetermined pressure that is selectable using pressure regulator 434. The selection of each source of test fluid in turn is accomplished using selector 446. Second source 424 is selected and pushbutton 448 is actuated to supply a stream of atomized dye penetrant solution from second source 424 to spray head 402, where the dye penetrant solution is atomized with an atomizing fluid, usually air, but may be other fluids. Actuating pushbutton 448 energizes the solenoid valve associated with the selected test fluid and the solenoid associated with the atomizing fluid. A rinsing agent from third source 428 and a developer from fourth source 432 are also applied similarly. At various times during the test procedure, a drying fluid may be selected and applied. The drying fluid may be a stream of compressed air or may be another fluid applied to blade 44. A power supply 452 is mounted within control box 412 and is configured to be coupled to a source of power external to control box 412 through power cord 454 or may be powered through an internal battery 456 or other storage device.

FIG. 5 is a flow chart of an exemplary method 500 of dye penetrant testing that may be used to test and/or inspect blades 44 (shown in FIG. 3). The method includes positioning 502 an outlet of an inspection fluid wand proximate a component to be inspected. In the exemplary embodiment, the component to be inspected is a blade of a gas turbine engine. The blade is positioned within the gas turbine engine amongst rows of blades aligned circumferentially about a disk. The blades in rows that are positioned downstream from a gas turbine engine inlet may be difficult to reach to perform an inspection and/or test to assess the condition of the blade. In the exemplary embodiment, a dye penetrant test includes spraying an atomized mixture of the test fluids used in the dye penetrant test onto a blade that, without the use of the various embodiments of the present invention, would be inaccessible for the test. The method also includes selecting 504 an inspection fluid source from a plurality of inspection fluid sources. In the exemplary embodiment, a solvent or cleaner is used to clean the blade, a rinse agent and a drying fluid is used to further prepare the blade for testing, a dye penetrant is sprayed onto the blade and allowed to soak into any cracks present in the blade, the blade is rinsed, and developer is applied to aid in visually inspecting the blade. Other embodiments of the method include various sequences of steps of applying different inspection fluids according to predetermined protocols. Flow is initiated 506 for at least one of an atomizing fluid and an inspection fluid to a mixing box in flow communication with the inspection fluid wand. The mixing box includes one or more venturis or internal shapes that promote mixing of the selected fluid and an atomizing fluid. The mixing box may include an eductor to suction the selected fluid into the mixing box when the fluid sources are non-pressurized. The flow of atomized inspection fluid is channeled 508 to the component to be inspected.

It will be appreciated that a technical effect of the configurations of the present invention described herein is the remote and sequential operation of test and/or inspection equipment.

The above-described embodiments of a dye penetrant test system provide a cost-effective and reliable means for inspecting and/or servicing equipment. More specifically, the dye penetrant test system includes a selectable quantity of different test fluids that are sequentially selected and applied to a workpiece, for example, a turbine blade that remains installed on a turbine rotor in an assembled machine, and to facilitate performing a test/or inspection remotely. As a result, the methods and apparatus described herein facilitate testing in a cost-effective and reliable manner.

Exemplary embodiments of dye penetrant test systems are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. An in-situ inspection system comprising:
  a plurality of sources of inspection fluids;

a source of an atomizing fluid;
a control panel comprising a plurality of flow control valves configured to control a flow of at least one of the inspection fluids and the atomizing fluid;
a mixing box configured to mix at least one of the inspection fluids with the atomizing fluid, wherein at least one of said plurality of sources of inspection fluids is at least one of pressurized prior to selecting the flow and educed in the mixing box; and
a spray tubing coupled to said mixing box for channeling the mixed fluid to a test head.

2. An in-situ inspection system in accordance with claim 1 wherein said inspection fluid comprises a liquid.

3. An in-situ inspection system in accordance with claim 1 wherein said mixing box is configured to educt a predetermined proportion of inspection fluid with respect to the atomizing fluid.

4. An in-situ inspection system in accordance with claim 1 wherein said plurality of sources of inspection fluid comprises at least one of a cleaner, a penetrant, a rinse agent, and a developer.

5. An in-situ inspection system in accordance with claim 1 wherein said control panel comprises a remote pendant configured to control a flow of at least one of the plurality of inspection fluids and the atomizing fluid.

6. An in-situ inspection system in accordance with claim 1 wherein said control panel comprises a flow control to adjust a proportion of the inspection fluid with respect to the atomizing fluid.

7. An in-situ inspection system in accordance with claim 1 wherein said mixing box further comprises a discharge wand configured to channel an atomized mixture that includes the inspection fluid to a component to be inspected.

8. A dye penetrant test system comprising:
a source of a plurality of inspection fluids;
a source of atomizing fluid;
a flow control associated with each of the plurality of inspection fluids;
a mixing box configured to mix at least one of the inspection fluids with the atomizing fluid, wherein at least one of said plurality of sources of inspection fluids is at least one of pressurized prior to selecting the flow and educed in the mixing box;
a selector configured to control a flow of at least one of the plurality of inspection fluids from said source of the plurality of inspection fluids to said mixing box; and
a spray tubing coupled to said mixing box for channeling the atomized fluid to a test head.

9. A dye penetrant test system in accordance with claim 8 wherein at least one of said plurality of inspection fluids comprises a liquid.

10. A dye penetrant test system in accordance with claim 8 wherein said mixing box is configured to educt a predetermined proportion of inspection fluid with respect to the atomizing fluid.

11. A dye penetrant test system in accordance with claim 8 wherein said source of a plurality of inspection fluids comprises at least one of a source of a cleaner, a source of a penetrant, a source of a rinse agent, and a source of a developer.

12. A dye penetrant test system in accordance with claim 8 further comprising a remote pendant configured to control a flow of at least one of the inspection fluid and the atomizing fluid.

13. A dye penetrant test system in accordance with claim 8 wherein said flow control is configured to adjust a proportion of the inspection fluid with respect to the atomizing fluid.

14. A dye penetrant test system in accordance with claim 8 wherein said mixing box further comprises a discharge wand configured to channel an atomized mixture that includes the selected inspection fluid to a component to be inspected.

15. A method of dye penetrant testing comprising:
selecting an inspection fluid source from a plurality of inspection fluid sources;
initiating a flow of at least one of an atomizing fluid and an inspection fluid to a mixing box, wherein the plurality of inspection fluid sources are at least one of pressurized prior to said initiating the flow, and educed in the mixing box; and
channeling a flow of atomized inspection fluid via a spray tubing coupled to the mixing box to the component to be inspected.

16. A method in accordance with claim 15 wherein selecting an inspection fluid source comprises sequentially selecting individual ones of the plurality of inspection fluid sources such that a plurality of different inspection fluids is channeled to the component in a selected sequence.

17. A method in accordance with claim 16 wherein sequentially selecting individual ones of the plurality of inspection fluid sources comprises automatically sequentially selecting individual ones of the plurality of inspection fluid sources using a predetermined protocol.

18. A method in accordance with claim 15 wherein pressurizing at least one of the plurality of inspection fluid sources comprises pressurizing at least one of the plurality of inspection fluid sources using a compressed gas.

19. A method in accordance with claim 15 wherein pressurizing at least one of the plurality of inspection fluid sources comprises pressurizing at least one of the plurality of inspection fluid sources using a pump.

20. A method in accordance with claim 15 wherein initiating a flow of at least one of an atomizing fluid and an inspection fluid comprises opening a fluid path between at least one of the plurality of inspection fluid sources and the atomizing fluid, and the outlet of the fluid inspection wand.

21. A method in accordance with claim 15 wherein the component to be inspected includes at least one surface to be inspected, and wherein channeling a flow of atomized inspection fluid to the component to be inspected comprises manipulating the outlet of the inspection fluid wand such that the atomized inspection fluid is channeled to substantially all of the surface to be inspected.

* * * * *